US011610305B2

(12) United States Patent
Ferrantelli et al.

(10) Patent No.: US 11,610,305 B2
(45) Date of Patent: Mar. 21, 2023

(54) METHOD AND SYSTEM FOR POSTURAL ANALYSIS AND MEASURING ANATOMICAL DIMENSIONS FROM A RADIOGRAPHIC IMAGE USING MACHINE LEARNING

(71) Applicant: POSTURE CO., INC., Trinity, FL (US)

(72) Inventors: Joseph Ralph Ferrantelli, Trinity, FL (US); Douglas Boberg, Dunedin, FL (US)

(73) Assignee: POSTURECO, INC., Trinity, FL (US)

( * ) Notice: Subject to any disclaimer, the term of this patent is extended or adjusted under 35 U.S.C. 154(b) by 100 days.

(21) Appl. No.: 17/073,523

(22) Filed: Oct. 19, 2020

(65) Prior Publication Data
US 2021/0118134 A1 Apr. 22, 2021

Related U.S. Application Data

(60) Provisional application No. 62/916,414, filed on Oct. 17, 2019.

(51) Int. Cl.
*G06K 9/00* (2022.01)
*G06T 7/00* (2017.01)
(Continued)

(52) U.S. Cl.
CPC .......... *G06T 7/0012* (2013.01); *G06K 9/6256* (2013.01); *G06K 9/6262* (2013.01);
(Continued)

(58) Field of Classification Search
CPC ......... G06T 7/0012; G06T 2207/10116; G06T 2207/20081; G06T 2207/20084;
(Continued)

(56) References Cited

U.S. PATENT DOCUMENTS 3,520,293 A 7/1970 Atherholt
3,659,494 A 5/1972 Philbrick et al.
(Continued)

FOREIGN PATENT DOCUMENTS

WO 2012/092167 A1 7/2012

OTHER PUBLICATIONS

Apr. 1, 2021 Notice of Allowance issued in U.S. Appl. No. 16/407,829.
(Continued)

*Primary Examiner* — Xin Jia
(74) *Attorney, Agent, or Firm* — Oliff PLC

(57) ABSTRACT

A method for use of machine learning in computer-assisted anatomical prediction. The method includes identifying with a processor parameters in a plurality of training images to generate a training dataset, the training dataset having data linking the parameters to respective training images, training at least one machine learning algorithm based on the parameters in the training dataset and validating the trained machine learning algorithm, identifying with the processor digitized points on a plurality of anatomical landmarks in a radiographic image of a person's skeleton displayed on a screen by determining anatomical relationships of adjacent bony structures as well as dimensions of at least a portion of a body of the skeleton in the displayed image using the validated machine learning algorithm and a scale factor for the displayed image, and making an anatomical prediction of the person's skeletal alignment based on the determined anatomical dimensions and a known morphological relationship.

22 Claims, 10 Drawing Sheets

(51) Int. Cl.
*G06K 9/62* (2022.01)
*G06N 3/08* (2023.01)
*G16H 30/20* (2018.01)

(52) U.S. Cl.
CPC .............. *G06N 3/08* (2013.01); *G16H 30/20* (2018.01); *G06T 2207/10116* (2013.01); *G06T 2207/20081* (2013.01); *G06T 2207/20084* (2013.01); *G06T 2207/30012* (2013.01); *G06V 2201/033* (2022.01)

(58) Field of Classification Search
CPC . G06T 2207/30012; G06T 2207/10081; G06T 2207/10088; G06T 2207/20101; G06T 2207/20121; G06T 2207/20124; G06T 2207/20132; G06T 2207/30008; G06T 7/60; G06K 9/6256; G06K 9/6262; G06K 9/6273; G06N 3/08; G06N 3/0454; G06N 3/084; G16H 30/20; G16H 30/40; G16H 50/20; G16H 50/70; G06V 2201/033; G06V 10/82
See application file for complete search history.

(56) References Cited

U.S. PATENT DOCUMENTS

| | | | |
|---|---|---|---|
| 4,603,486 A | 8/1986 | Moroney et al. | |
| 4,635,198 A | 1/1987 | Hohlweck et al. | |
| 4,786,925 A | 11/1988 | Landwehr | |
| 5,082,001 A | 1/1992 | Zannier et al. | |
| 5,947,742 A | 9/1999 | Katayama | |
| 6,231,527 B1 | 5/2001 | Sol | |
| 6,411,275 B1 | 6/2002 | Hedberg | |
| 6,423,015 B1 | 7/2002 | Winkenbach et al. | |
| 6,751,410 B1 | 6/2004 | Stavely | |
| 7,077,813 B2 | 7/2006 | Grace | |
| 7,335,167 B1 | 2/2008 | Mummy | |
| 7,366,559 B2 | 4/2008 | Taicher et al. | |
| 7,374,536 B1 | 5/2008 | Taylor | |
| 7,478,009 B2 | 1/2009 | Cabrera et al. | |
| 7,683,915 B2 | 3/2010 | Gunji | |
| 7,742,073 B1 | 6/2010 | Cohen-Solal et al. | |
| 7,761,233 B2 | 7/2010 | Schott et al. | |
| 7,796,871 B2 | 9/2010 | Park et al. | |
| 7,796,872 B2 | 9/2010 | Sachs et al. | |
| 7,876,320 B2 | 1/2011 | Marugame | |
| 7,957,784 B2 | 6/2011 | Voth et al. | |
| 8,209,240 B2 | 6/2012 | Ryu et al. | |
| 8,721,567 B2 | 5/2014 | Ferrantelli | |
| 9,788,759 B2 | 10/2017 | Ferrantelli | |
| 9,801,550 B2 | 10/2017 | Ferrantelli | |
| 10,692,602 B1* | 6/2020 | Nguyen | G06T 7/11 |
| 2002/0116990 A1 | 8/2002 | Claussen | |
| 2003/0076408 A1 | 4/2003 | Dutta | |
| 2004/0186395 A1 | 9/2004 | Vastano | |
| 2006/0072019 A1 | 4/2006 | Stavely et al. | |
| 2006/0203131 A1 | 9/2006 | Gunji | |
| 2007/0083384 A1 | 4/2007 | Geslak et al. | |
| 2007/0135737 A1 | 6/2007 | Vastano | |
| 2007/0230829 A1 | 10/2007 | Sirohey et al. | |
| 2008/0009773 A1 | 1/2008 | Harrison et al. | |
| 2008/0030464 A1 | 2/2008 | Sohm et al. | |
| 2008/0031512 A1 | 2/2008 | Mundermann et al. | |
| 2008/0044169 A1 | 2/2008 | Wernersson | |
| 2008/0200841 A1 | 8/2008 | Di Mascio et al. | |
| 2009/0046140 A1 | 2/2009 | Lashmet et al. | |
| 2009/0062693 A1 | 3/2009 | Woolfson et al. | |
| 2009/0262989 A1 | 10/2009 | Kozakaya | |
| 2010/0002015 A1 | 1/2010 | Handa | |
| 2010/0004539 A1 | 1/2010 | Chen et al. | |
| 2010/0077857 A1 | 4/2010 | Ye | |
| 2010/0078479 A1 | 4/2010 | Epshteyn | |
| 2010/0138194 A1 | 6/2010 | You et al. | |
| 2010/0141784 A1 | 6/2010 | Yoo | |
| 2011/0009776 A1 | 1/2011 | Woolfson et al. | |
| 2011/0015513 A1 | 1/2011 | Mura Yanez | |
| 2011/0135165 A1 | 6/2011 | Wechsler et al. | |
| 2011/0251903 A1 | 10/2011 | Ryu et al. | |
| 2012/0040717 A1 | 2/2012 | Levy et al. | |
| 2012/0165647 A1 | 6/2012 | Kang et al. | |
| 2012/0165648 A1 | 6/2012 | Ferrantelli | |
| 2012/0235993 A1 | 9/2012 | Kim | |
| 2013/0324850 A1 | 12/2013 | Petruzzelli et al. | |
| 2014/0031700 A1 | 1/2014 | Ferrantelli | |
| 2014/0267611 A1 | 9/2014 | Kennett et al. | |
| 2019/0103190 A1* | 4/2019 | Schmidt | G16H 30/40 |
| 2019/0110753 A1 | 4/2019 | Zhang et al. | |
| 2019/0272890 A1 | 9/2019 | Aliper et al. | |
| 2019/0318261 A1 | 10/2019 | Deng et al. | |
| 2020/0161005 A1* | 5/2020 | Lyman | G06F 16/245 |
| 2020/0210472 A1 | 7/2020 | Das et al. | |
| 2021/0049756 A1* | 2/2021 | He | G06T 7/11 |

OTHER PUBLICATIONS

Feb. 24, 2015 Search Report Issued in Canadian Application No. 2,822,244.
Feb. 25, 2016 Office Action issued in U.S. Appl. No. 14/037,526.
Sep. 28, 2016 Office Action issued in U.S. Appl. No. 14/037,526.
Jan. 20, 2017 Office Action issued in U.S. Appl. No. 14/037,526.
Dec. 16, 2016 Office Action issued in U.S. Appl. No. 14/598,937.
Hodgdon, J.A. and M.B. Beckett. "Prediction of Percent Body Fat for U.S. Navy Men from Body Circumference and Height". Report No. 84-11, Naval Health Research Center, San Diego, CA, 26 pages.
Hodgdon, J.A. "Body Composition in Military Services: Standards & Methods". Report No. 90-21, Naval Health Research Center, San Diego, CA, 18 pages, 1990.
"The Army Weight Control Program". Army Regulation 600-9, Headquarters, Department of the Army, Washington, D.C., 55 pages, Nov. 27, 2006.
"Waist Circumference and Waist-Hip Ratio, Report of a WHO Expert Consultation" World Health Organization, Geneva, Switzerland, 14 pages, Dec. 8-11, 2008.
Department of Defense publication DODI 1308.3, 41 pages, Nov. 5, 2002.
Apr. 25, 2012 Search Report and Written Opinion issued in International Patent Application No. PCT/US2011/067111.
Jan. 9, 2013 Preliminary Report on Patentability issued in International Patent Application No. PCT/US2011/067111.
Nov. 20, 2020 Office Action Issued in U.S. Appl. No. 16/407,829.
U.S. Appl. No. 16/407,829, filed May 9, 2019 in the name of Ferrantelli et al.

* cited by examiner

FIG. 5

SPINAL BIOMECHANICS COMPARED TO NORMAL

| SEGMENTS ANALYZED | RRA NORMAL VALUES | RRA PATIENT VALUES | DIFFERENCE FROM NORMAL | SEGMENTAL TRANSLATIONS |
|---|---|---|---|---|
| C1 TO HORIZ. | -29.0° | -30.3° | 4.5% | |
| C2-C3 | -10.0° | -10.9° | 9.0% | -1.1mm |
| C3-C4 | -8.0° | 0.4° | 105.0% | -0.7mm |
| C4-C5 | -8.0° | 9.8° | 222.5% | 0.8mm |
| C5-C6 | -8.0° | 14.3° | 278.8% | 0.6mm |
| C6-C7 | -8.0° | -3.2° | 60.0% | -0.8mm |
| C7-T1 | -8.0° | -13.9° | 73.7% | -0.4mm |

RRA = RELATIVE ROTATIONAL ANGLE OF MEASUREMENT
*VALUES IN RED EXCEED ESTABLISHED NORMAL

| GLOBAL ANALYSIS | NORMAL VALUE | PATIENT VALUES | DIFF. FROM NORMAL |
|---|---|---|---|
| ARA C2-C7 (SEGMENTAL SUM) | -42° | 10.4° | 124.8% |
| ARA C2-C7 (GLOBAL) | -42° | 10.3° | 124.5% |
| TRANSLATION C2-C7 | 0 mm | 17.8 mm | 17.8mm |
| C7 POST TANGENT TO VERT | 21.5° | 2.0° | 90.7% |
| T1 POST TANGENT TO VERT | 26.5° | 11.8° | 55.5% |
| CBP C1-S1 | 0 mm | 55.6 mm | 55.6 mm |
| C7 CENTROID - S1 POST SUP. | 0 mm | 23.8 mm | 23.8 mm |
| T1 POST INF - S1 POST INF | 0 mm | 19.7 mm | 19.7 mm |

ARA = ABSOLUTE ROTATION ANGLE OF MEASUREMENT
DIRECTION OF MEASURED DISPLACEMENTS ARE INDICATED USING THE RIGHT-HAND CARTESIAN COORDINATE SYSTEM METHOD IN BIOMECHANICS. CONSEQUENTLY A "-" NEGATIVE SIGN PRECEDING A MEASURED VALUED INDICATES POSTERIOR TRANSLATION FOR LINEAR MOVEMENTS; AND A "-" PRECEDING ANGULAR MEASUREMENTS INDICATE RELATIVE SEMENTAL OR GLOBAL EXTENSION ROTATIONAL MOVEMENT.

6/29/2013 INITIAL X-RAY

METHOD AND SYSTEM FOR POSTURAL ANALYSIS AND MEASURING ANATOMICAL DIMENSIONS FROM A RADIOGRAPHIC IMAGE USING MACHINE LEARNING

This application claims priority to Provisional Application No. 62/916,414, filed Oct. 17, 2019. The entire contents of the prior application are hereby incorporated by reference herein in their entirety.

TECHNICAL FIELD

This application relates to a method and system for using machine learning algorithms in the measuring of anatomical dimensions from a medical image such as, for example, a radiographic image, on a mobile device or computer. Disclosed embodiments relate particularly to postural screening, measurements for biomechanics and line drawing assessments for researchers, chiropractors, orthopedists, radiologist and the like.

BACKGROUND

In chiropractic practice, standard of care requires the clinician to "hand draw" on x-rays and to measure spinal subluxations using a protractor or templates such as the CBP® OXI and Elliptical Normal Templates. Even when doctors upgrade to digital x-ray solutions, they are left with very limited analysis tools built into their PACs, which unfortunately take considerable time to utilize—leaving less time for patient care.

X-ray line drawing is not only a tedious task, but also is very time consuming, which is why many in the profession fail to identify crucial spinal subluxations. For most doctors, they must analyze films themselves, which places a burden on the doctor, taking time away from adjusting patients. This leaves most to resort to simply using only the briefest of lines (like only using the CBP® normal templates for patient education which are plastic templates allowing constructing of lines and measurements where a practitioner must physically overlay and draw on a hard copy of an x-ray).

Sometimes, the doctor will fall victim of "believing" that they are good enough to treat patients without a thorough segmental and global analysis of spinal alignment. However, many of the patients who failed to "respond" to care may be secondary to the clinician failing to recognize the significant yet subtle segmental vertebral hyper-extension or hyper-flexion buckling (2nd and 3rd harmonics) of the sagittal curves on lateral views. If the doctor does not identify the displacement, correction becomes unlikely.

Systems that allow analysis of Digital Imaging and Communications in Medicine (DICOM) radiographic (i.e., x-ray) files from a digital x-ray system are known. DICOM images are used throughout medicine as a standard for imaging modalities such as radiography, ultrasonography, computed tomography (CT), magnetic resonance imaging (MRI), and radiation therapy. DICOM includes protocols for image exchange (e.g., via portable media such as DVDs), image compression, 3-D visualization, image presentation, and results reporting.

While the use of such imagery, including radiographic imagery, is known, conventional systems and methods do currently employ any systematic learning procedures for making the systems and methods of analyzing medical images "smarter." Recently, the inventors have employed machine learning techniques in developing systems and practicing methods for deriving an anatomical prediction that address these and other drawbacks.

Commonly-assigned U.S. patent application Ser. No. 16/407,829, which is hereby incorporated by reference in its entirety, provides improved methods and systems for use of machine learning in computer-assisted anatomical prediction using two-dimensional and three-dimensional images. Machine learning algorithms allow computer systems to solve a variety of problems, answer questions and perform other tasks based not solely upon pre-programmed instructions, but also upon inferences developed from training data. The training data can be used to "train" the machine learning algorithms by creating representations and generalizations that can then be applied to additional data in the future. The weights and parameters of the different representations and generalizations are "learned" by machine learning.

The inventors have looked to using machine learning algorithms and classifier software implemented in a specialized computer program to enhance, among other things, (1) digitizing points on a plurality of anatomical landmarks on the displayed radiographic images, (2) determining linear anatomical dimensions of at least a portion of a body of a person in the displayed radiographic images using the digitized points and a scale factor for the displayed radiographic images, and (3) making measurement predictions of the person based on the determined linear and angular anatomical dimensions and a known a morphological relationship. These algorithms and classifiers utilize machine learning techniques to develop a model for distinguishing and measuring various body dimensions. The training data consisting of image data may be annotated by a domain expert (such as a physiologist) and fed into the classifier, and the classifier analyzes the training data to identify patterns in the data that indicate when a given sample corresponds to a known dimensions stored in a database. After the classifier has been trained, a set of similarly annotated validation data is typically used to test the accuracy of the classifier. This type of machine learning is known as "supervised learning," since the training and validation data is annotated by a human "supervisor" or "teacher." Unsupervised learning is also contemplated.

Use of machine learning algorithms has shown to provide faster, more accurate and more precise identification of anatomical landmarks than previously possible. They do so, in part, based on the ability to identify patterns in a myriad of data that are not discernable to the human eye or capable of being processed by any known process, mental or otherwise.

SUMMARY

Disclosed embodiments use machine learning to provide several advantages including: (1) enhanced ability to compare a subject's spine to normal from digital x-ray, CT and/or MRI images of the spine and pelvis. In practice, these areas may fall under the following x-ray views: AP and lateral cervical in neutral position as well as with flexion and extension postures, AP Open Mouth Cervical, Nasium, Vertex, AP and lateral thoracic with flexion and extension, and AP and lateral lumbar films with or without flexion and extension postures, AP or PA Ferguson sacral base views along with Modified Ferguson projections as well as femur head x-ray views in order to obtaining true anatomical leg length inequality, AP and lateral full spine and flexion/extension stress views, (2) allowing a subject's x-rays to be available in and compared to a multitude of records in a master database, (3) enhanced ability to compare a subject's subluxations at each level to normal and the percentage loss or gain from normal calculated automatically measuring all segmental relative rotational angles and the global absolute rotational angles in degrees along with all translational distances in, for example, centimeters, millimeters or percentages of translation relative to the vertebrae below along with corresponding angular measurements both intersegmental and global angulations of all segments, (4) allowing for superimposition of normal and/or ideal spinal curves (using any color) and highlights George's line (subject's spinal position) on their digital x-rays, (5) applying and overlaying a normal and/or ideal spinal models on digital images, (6) comparing a subject's pre- and post-care films with percentage improvement at each level of their spine, or conversely their worsening if they had a traumatic event such as a motor vehicle crash, and (7) objectively measuring spinal instability crucial for calculating impairment ratings.

In a first embodiment, there is provided a method for use of machine learning in computer-assisted anatomical prediction. The method comprises identifying with a processor parameters in a plurality of training images to generate a training dataset, the training dataset having data linking the parameters to respective training images, training at least one machine learning algorithm based on the parameters in the training dataset and validating the trained machine learning algorithm, identifying with the processor digitized points on a plurality of anatomical landmarks in a radiographic image of a person displayed on a digital touch screen or traditional computer with a mouse pointer by determining linear anatomical dimensions of at least a portion of a body of the person in the displayed image using the validated machine learning algorithm and a scale factor for the displayed image, and making an anatomical prediction of the person based on the determined linear anatomical dimensions and a known morphological relationship.

In another embodiment, there is provided a system for use of machine learning in computer-assisted anatomical prediction. The system comprises a memory configured to store at least one machine learning algorithm and datasets, a processor programed to: (i) identify parameters in a plurality of training images to generate a training dataset, the training dataset having data linking the parameters to respective training images, (ii) train the machine learning algorithm based on the parameters in the training dataset and validate the trained machine learning algorithm, (iii) identify digitized points on a plurality of anatomical landmarks in a radiographic image of a person displayed on a digital touch screen by determining linear anatomical dimensions of at least a portion of a body of the person in the displayed image using the validated machine learning algorithm and a scale factor for the displayed image, and (iv) make an anatomical prediction of the person's spine based on the determined linear and angular anatomical dimensions and a known morphological relationship.

In another embodiment, there is provided non-transitory computer readable storage medium having stored therein a program to be executable by a processor for use of machine learning in computer-assisted anatomical prediction. The program causes the processor to execute identifying with a processor parameters in a plurality of training images to generate a training dataset, the training dataset having data linking the parameters to respective training images, training at least one machine learning algorithm based on the parameters in the training dataset and validating the trained machine learning algorithm, identifying with the processor digitized points on a plurality of anatomical landmarks in a radiographic image of a person displayed on a digital touch screen by determining linear anatomical dimensions of at least a portion of a body of the person in the displayed image using the validated machine learning algorithm and a scale factor for the displayed image, and making an anatomical prediction of the person based on the determined linear anatomical dimensions and a known morphological relationship.

BRIEF DESCRIPTION OF DRAWINGS

FIG. 5 is an analysis report according to an embodiment.

DETAILED DESCRIPTION

Figure 1:
FIG. 1 is a radiographic image of a cervical portion of the human spine from a lateral viewpoint.

According to embodiments, there are provided systems and methods of using machine learning algorithms to derive an anatomical prediction using a known morphological relationship and a programmed apparatus including a digital touch screen display or traditional computer based system with a mouse or other pointer system and a device configured to acquire a radiographic image of a person on the screen display. In embodiments, the systems and methods may comprise acquiring at least one radiographic image of a person on the screen, digitizing points on a plurality of anatomical landmarks on the displayed radiographic image, calculating a measurement of at least a portion of a body of a person in the displayed radiographic image using at least the digitized points on the displayed radiographic image, and making an anatomical prediction based on the calculated measurement and a known morphological relationship. One such system is the POSTURERAY® EMR software system available from PostureCo, Inc.

The disclosed system further includes means for making an anatomical prediction using the measured dimensions and a known morphological relationship. Known mathematical formulae expressed in the computer program of the device relate the measured dimensions to the anatomical prediction. According to embodiments, the anatomical prediction includes at least one of length, angle, and deviation from normal which may be displayed on the display screen. In a further embodiment a postural displacement is predicted from the measured dimensions and known morphological relationship.

Thus, disclosed embodiments include a method of deriving an anatomical prediction using a known morphological relationship and a programmed apparatus including a digital touch screen display and means for acquiring a radiographic image of a person on the digital touch screen display, the method comprising acquiring a radiographic image of a person on the digital touch screen display, digitizing points on a plurality of anatomical landmarks on the displayed image, determining linear anatomical dimensions of the person's body using the digitized points and a scale factor for the displayed image, and making an anatomical prediction using the determined linear anatomical dimensions and a known morphological relationship. In one embodiment, the anatomical prediction is a postural displacement from normal.

To further exemplify the use of the radiographic images according to embodiments, it is noted that often chiropractors or other health care providers are reluctant on giving care plans or explanations as to why it will take time to alleviate symptoms, correct the underlying problem, and maintain wellness. Traditionally, when conditions are diagnosed, there have been validated courses of care for a specific condition. According to embodiments, chiropractors or other health care professionals such as, for example, orthopedists and radiologists can provide validated evidence as to what the scientific research demonstrates on a case-specific basis. This allows subjects to make a more informed decision about engaging in the appropriate care. Disclosed embodiments provide a machine-learning based tool to pass this validated information on to subjects, thereby significantly enhancing the quality of care.

In the disclosed embodiments, methods may comprise acquiring at least one (or more) radiographic views of the person as images on the digital touch screen display or traditional computer with pointing system such as a mouse or pen, which can be rotated to provide each of said at least one x-ray view, digitizing points on anatomical spinal or other bony landmarks on each displayed image and determining linear and angular anatomical alignment and dimensions where applicable of the person's spine using the digitized points and a scale factor for each displayed image for making the anatomical prediction. In the disclosed embodiments the views acquired include at least a front view and/or a side view of the person and/or a radiographic image of the person which can be rotated to provide each of the front and side views.

An embodiment particularly relating to measuring dimensions of an x-ray of the human spine using a radiographic image is disclosed but the disclosure should not be so limited. It will be understood that the disclosed methods and systems may be applied to other body structures and/or medical images.

The improved efficient screening method according to the example embodiments comprises acquiring a radiographic image of a patient on a display screen having an array of pixels, determining a pixel to distance ratio for the displayed image, and calculating a spinal displacement of the patient in the displayed image using the determined ratio. According to the disclosed method, a known linear distance and angular measurements in the displayed image and the number of display screen pixels spanning the distance are used in determining pixel to distance ratio, linear dimensions and angulations of bony alignment. The known linear distance in an example embodiment is calculated from DICOM metadata and pixel ratios. Alternately, or in addition as a secondary calibration, a marked distance can be provided in the acquired image of the patient's spine, as by the use of a annotation software or linear measurement if on plain film in a traditional sense, and in the image or other markings of a known distance apart, to provide a known linear distance. This linear annotated distance can be measured by the computer system to use a scaling factor when traditional DICOM metadata is not present for calibration methods for radiographic images.

The x-ray screening method in example embodiments further includes scaling the size of the image relative to the display screen to normalize the known linear distance in the image to a display screen reference distance corresponding to a known number of pixels for determining the pixel to distance ratio. According to a disclosed method, at least one reference line is provided over the displayed image to demark the display screen reference distance.

The method as disclosed herein further includes displaying a reference line overlaid on the screen providing vertical, horizontal and center references, providing a corresponding reference line anchored to the displayed subject's image, and adjusting the image in the display so that the two reference lines are aligned before determining the pixel to distance ratio.

In disclosed embodiments, the method further includes displaying a reference line on the display screen over the acquired image, performing panning to center the image on the screen, and performing zooming to fit the image in the reference line before determining the pixel to distance ratio. Still further, the method comprises providing anatomical landmarks on the acquired image of the patient to facilitate calculating a postural displacement. The display screen is a touch screen for this purpose to identify coordinates for calculation of postural displacements by a CPU.

The capture and storage of radiographic images according to embodiments is not particularly limited and can be done using any suitable systems or methods known in the art. A system for performing postural screening according to the disclosed embodiments may comprise means for acquiring a radiographic image of a patient on a display screen having an array of pixels, means for determining a pixel to distance ratio for the displayed image and means for calculating a postural displacement of the patient in the displayed image using the determined ratio. The means for acquiring an image of a subject according to an example embodiment includes an image capture device for capturing a radiographic image of the person on the digital touch screen display. The system further includes means for panning a displayed image on the screen to center the image on the screen, and means for zooming to fit a displayed image in a reference line on the display screen. Means are provided for displaying at least one reference line over the displayed image to demark a display screen reference distance corresponding to a known number of pixels for determining the pixel to distance ratio.

The system of disclosed embodiments further includes means for displaying a reference line overlaid on the screen providing vertical, horizontal and center references, means for displaying a corresponding reference line anchored to the displayed subject's image, and means for aligning image and display screen reference lines before determining the pixel to distance ratio. The reference line may be, for example, a normal line such as the normal elliptical model. The system further includes means for providing anatomical landmarks on the acquired image of the subject to facilitate calculating a postural displacement.

Disclosed embodiments further include a machine-readable medium containing at least one sequence of instructions that, when executed, causes a machine to: calculate at least one postural displacement of a subject from a displayed image of the subject on a display screen having an array of pixels, using a determined pixel to distance ratio for the displayed image.

Disclosed embodiments generally provide a method for determining an anatomical measurement of the human body such as measuring the dimensions of the human body, and digitizing anatomical landmarks on a displayed radiographic image of the human body displayed on the device with established calibration methods for measuring dimensions of the human body. The embodiments provide a device or system using digitization of anatomical landmarks on a radiographic image with established calibration methods. The device/system is designed for measuring the dimensions of the human body and comprises a programmed device including a digital display, a touch screen in the example embodiments having an array of pixels and x-ray camera for acquiring a radiographic image of a person on the digital touch screen display, and means for digitizing anatomical landmarks on an image of a person displayed on the touch screen display for measuring dimensions of the human body.

Another embodiment enables the ability to derive the anatomical measurement such as the linear measurement or an angular measurement from the anterior, posterior and lateral aspects of a body part, and then calculate dimensions using mathematical equations.

Disclosed embodiments also enable recording a linear distance and subsequent anatomical calculations utilizing mathematical formulae which can also be tracked by software. The measurements can also be superimposed on the radiographic image of the person displayed on the device.

Another embodiment can produce reports for education on body posture and measurements. This could be used by clinicians, fitness professionals, health care professionals, or industry professionals or where an anatomical measurements need to be calculated by using prediction from digitizing anatomical points on/from a radiographic picture.

Once the images are obtained and digitized following protocols of the disclosed methods, digitization points on anatomical landmarks for purposes of posture, linear and anthropometric measurements can be performed. After these measurements are obtained, body ratios can be calculated to predict a person's alignment using well known anthropometric morphological relationships.

Embodiments can be used to calculate body dimensions, shape, posture, and deviation based on anatomical ratio relationship, and to track progress of linear, angular and anatomical measurements.

One embodiment is a skeletal screening method comprising acquiring subject information, acquiring a radiographic image of the subject, displaying a reference line overlaid on the acquired image for scaling the acquired image, providing panning to center the acquired image, providing zooming to fit the image within the displayed reference lines, for normalizing the subject's height or other calibration data as disclosed previously, determining a pixel to distance ratio using the acquired subject information and the normalized subject height, calculating postural displacements, and presenting a postural analysis. Aspects of the disclosed embodiments provide a postural screening method that may be implemented on a programmable device that incorporates a device's camera.

A method according to an embodiment includes a step of acquiring subject information, which may include, for example, accessing a database or prompting a user to enter information. Acquired information in may include, for example, height, weight, sex and age of the subject.

The method includes acquiring a radiographic image of the subject. By way of example, the radiographic image may be an image of the cervical portion of the subject's spine, as seen in FIG. 1.

A plurality of images may be acquired including, for example, a frontal image, a lateral image, and a dorsal image.

According to disclosed embodiments, the system may include accessing a data storage device. The data storage device may include, for example, a picture roll or album, which may contain a previously captured image of the subject.

The method may include a step of displaying an upper reference line and a lower reference line over a display of the radiographic image of the subject. The two spaced parallel lines being spaced apart a reference distance corresponding to a known number of pixels of screen. The displayed reference lines may be used as a reference for aligning or normalizing the images, which may require positioning or scaling. Hence, method may include a step of providing panning capability of the acquired image to a user, and a step of providing zoom capability of the acquired image to a user. The provided panning capability may allow a user to properly center or rotate images to fit in reference lines. The provided zoom capability may allow a user to properly size an acquired image to fit it within reference lines for normalizing the dimensions of the structure in the acquired image and establishing a corresponding pixel height. The method may include a step of determining a pixel-to-distance ratio, which may be a quotient calculated by dividing a pixel height of images divided by a known size of a body structure.

The method may include a step of providing for identification of the subjects anatomical landmarks, wherein a user may be prompted to identify locations of a plurality of anatomical landmarks on the acquired image of the patient by touching the touchscreen of the device to identify an anatomical landmark. The plurality of the landmarks may correspond, for example, to skeletal landmarks, bone markings, or joints. The identified plurality of landmarks may be used with the known pixel to distance ratio for the displayed image to calculate absolute distances and relative spatial positioning thereof, and may be used in an analysis of the subject's alignment. In an exemplary embodiment, the selection of anatomical landmarks may be on a plurality of images. The image of FIG. 2 depicts the digitized anatomical landmarks placed on the image of FIG. 1 for the purpose of making linear measurements in the lateral view of the subject.

Figure 2:
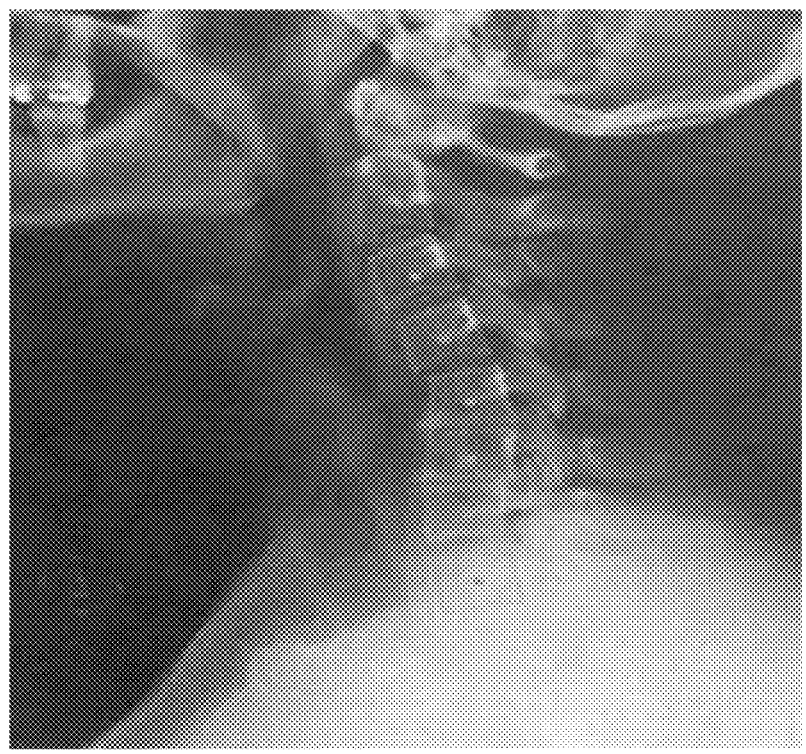
FIG. 2 is the radiographic image of FIG. 1 including digitized landmarks according to an embodiment.
Figure 3:
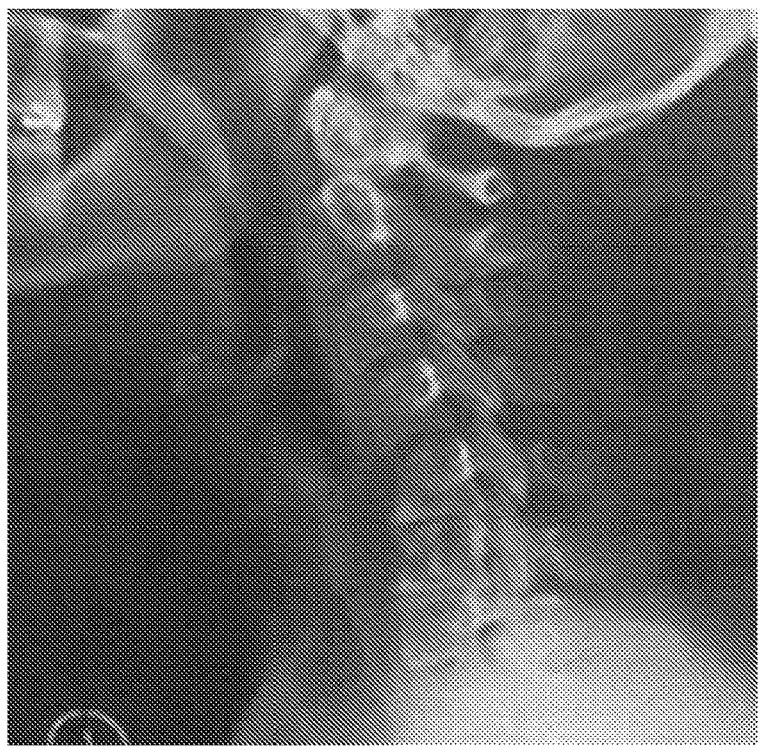
FIG. 3 is the radiographic image of FIG. 2 showing an overlay of the normal elliptical model according to an embodiment.

FIG. 3 illustrates the radiographic image of FIG. 2 showing the normal elliptical model overlaid on the image. In embodiments, the placement of the "normal" line is determined according to machine-learning algorithms disclosed herein.

Figure 4:
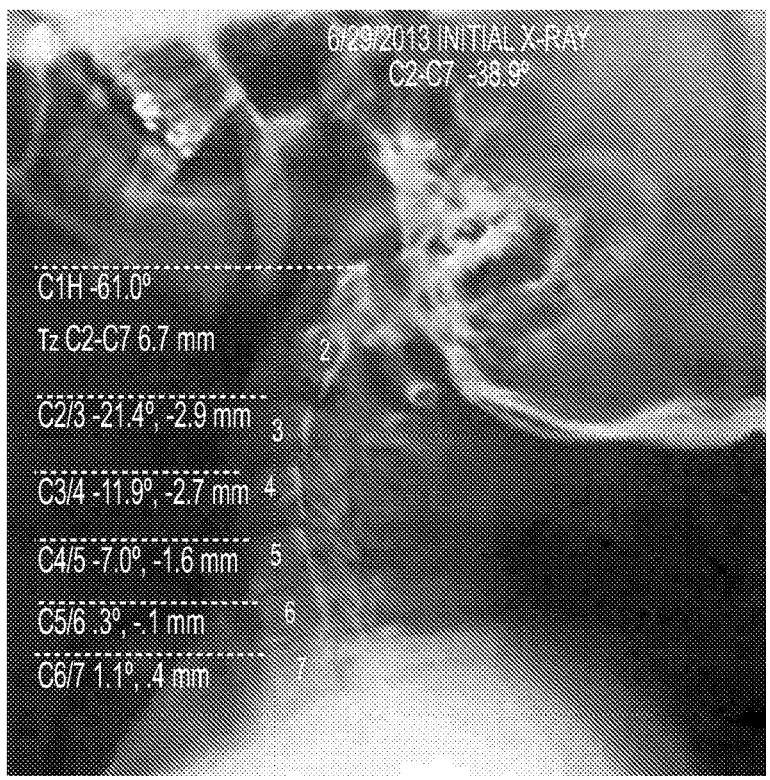
FIG. 4 is a radiographic image showing an overlay of data analysis points according to an embodiment.

The method may include a step of calculating postural displacements using the determined pixel to distance ratio. The displacements may include, for example, linear displacements and angular displacements relative to the "normal" line. These dimensions can then be overlaid on the displayed radiographic image, as seen in FIG. 4.

The method may include a step of presenting the resulting postural, spinal and or skeletal analysis in tabular or report format, as shown in FIG. 5. The spinal, skeletal or postural analysis may display, for example, the calculated linear or angular displacements and any deviation thereof from the normal or proper posture taking into account, for example, the subject's age, sex, height, and weight. The normal or proper alignment itself can be displayed over the displayed subject's radiographic image to provide a visual comparison.

Figure 6A:
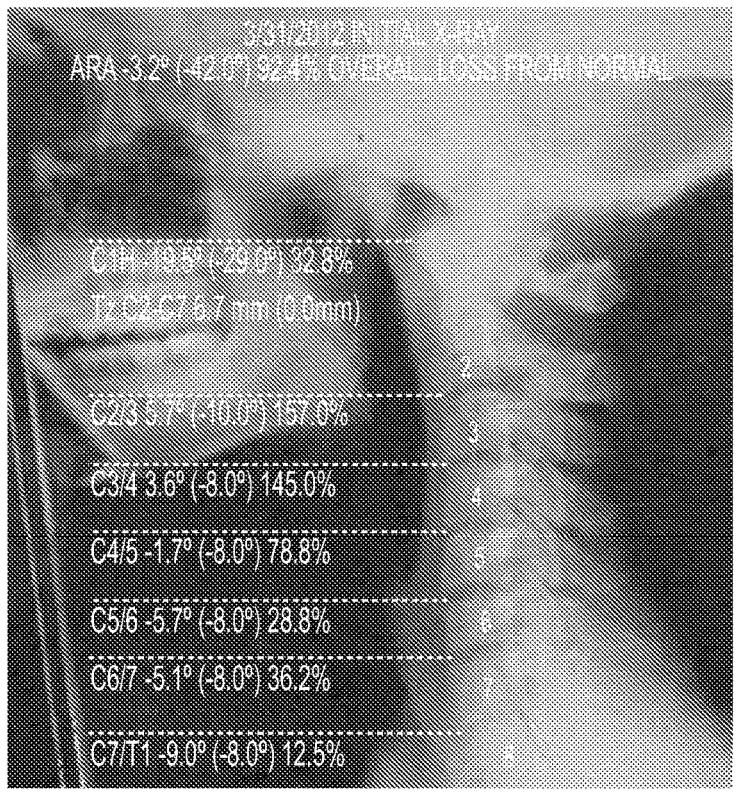
FIG. 6A is a radiographic image of a cervical portion of the human spine before treatment according to an embodiment.
Figure 6B:
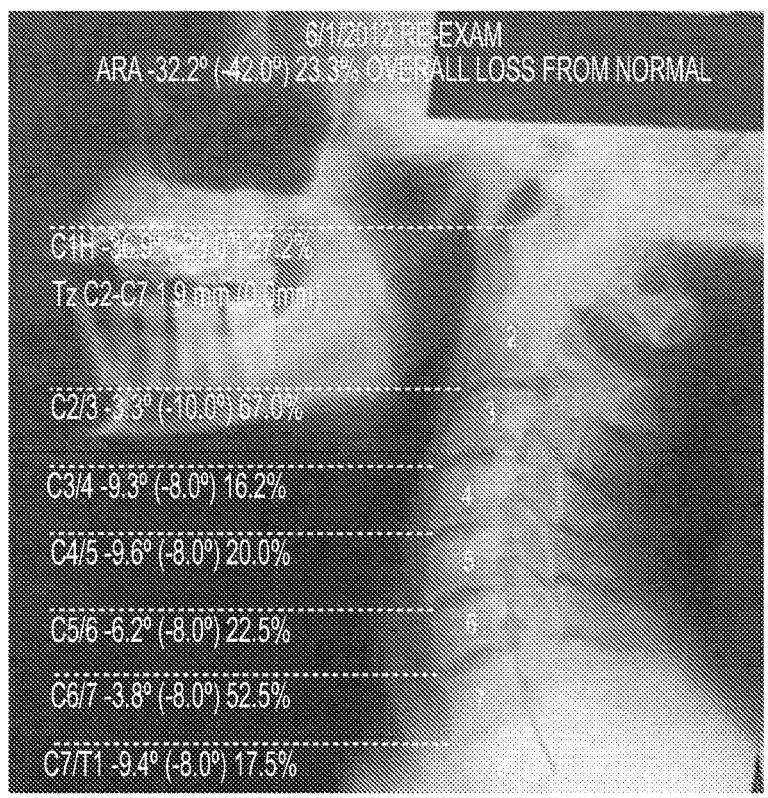
FIG. 6B is radiographic image of the cervical portion of the human spine in FIG. 6A after treatment according to an embodiment.

The method may include a tracking step of tracking the progress of a subject over time as shown in FIGS. 6A and 6B. In this regard, FIG. 6A illustrates a radiographic image of a cervical portion of the spine of subject after a traumatic event and before treatment. FIG. 6B shows the same portion of the spine of the subject post-treatment. As seen in FIG. 6B, the cervical portion of the spine tracks the shape of the normal elliptical model indicating the success of the treatment protocol.

Figure 7:
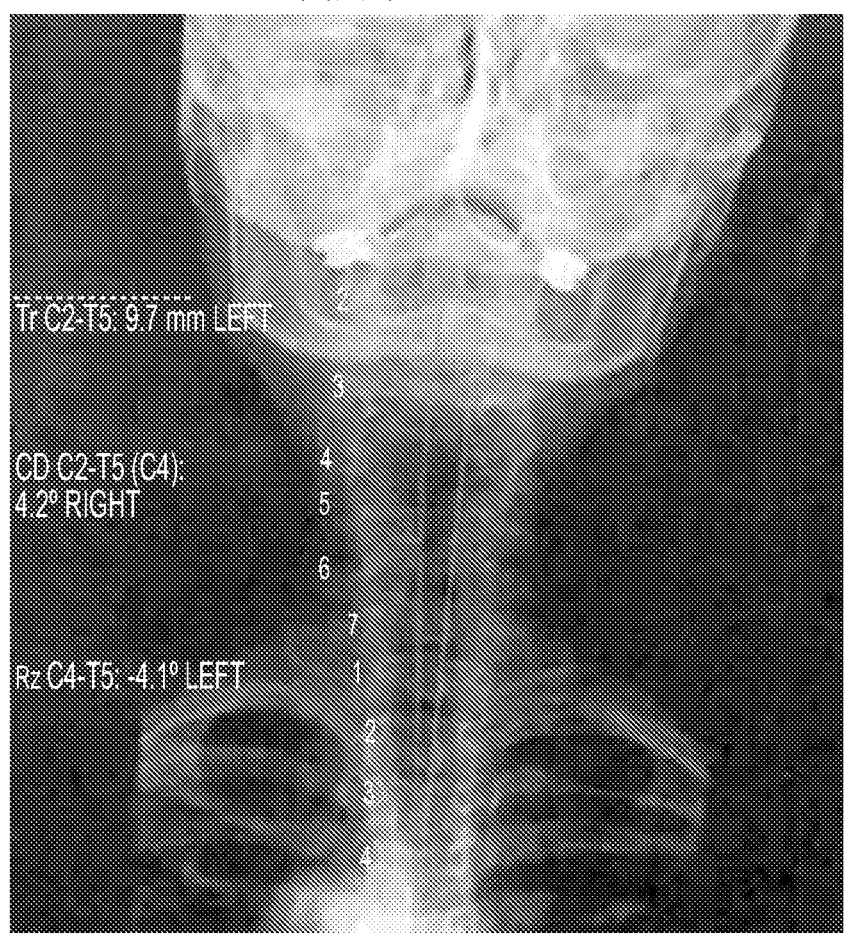
FIG. 7 is a radiographic image of a cervical portion of the human spine from a dorsal viewpoint showing an overlay of data analysis points and the normal line.
Figure 8:
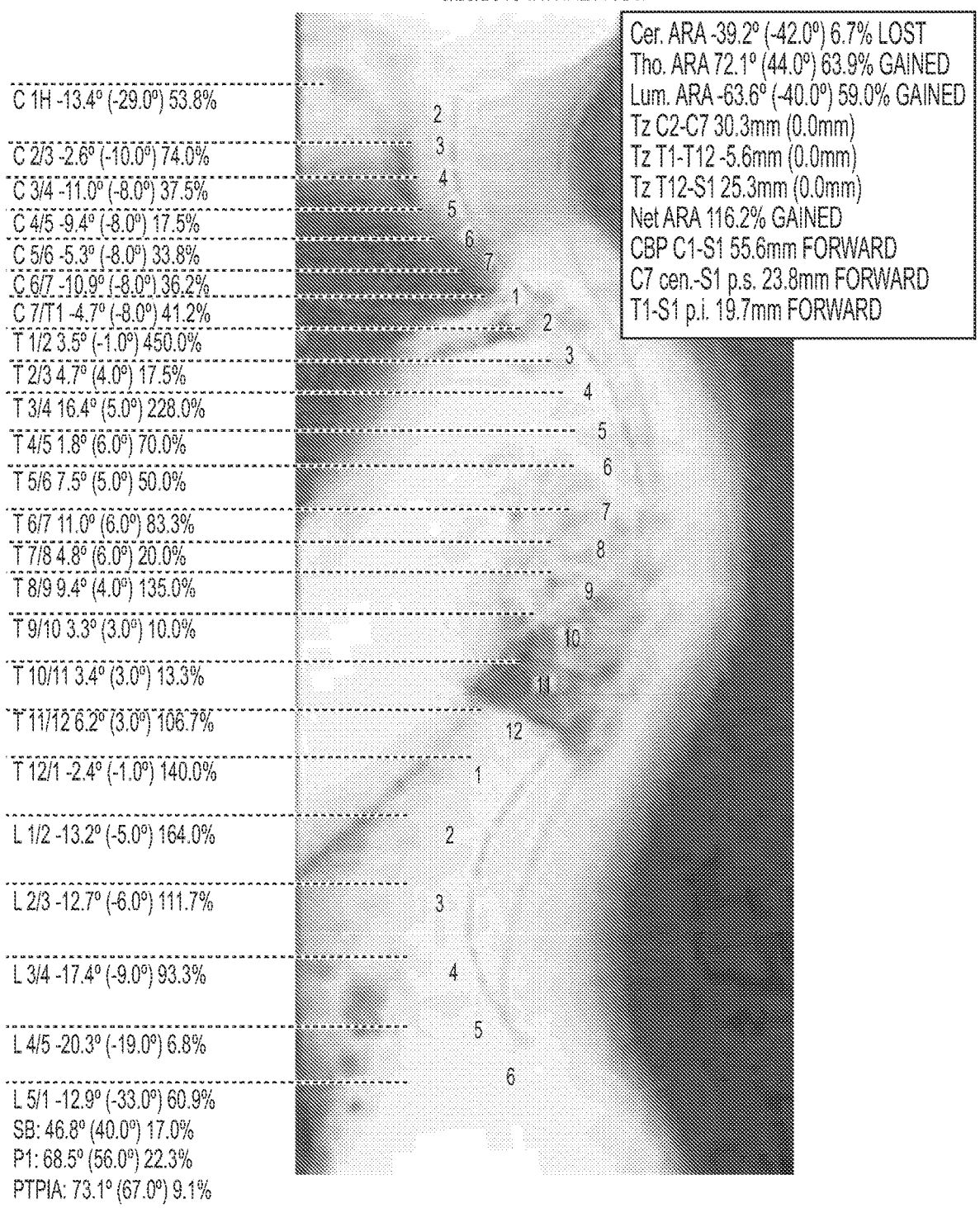
FIG. 8 is a radiographic image of the human spine from a lateral viewpoint showing an overlay of data analysis points and the normal line.
Figure 9:
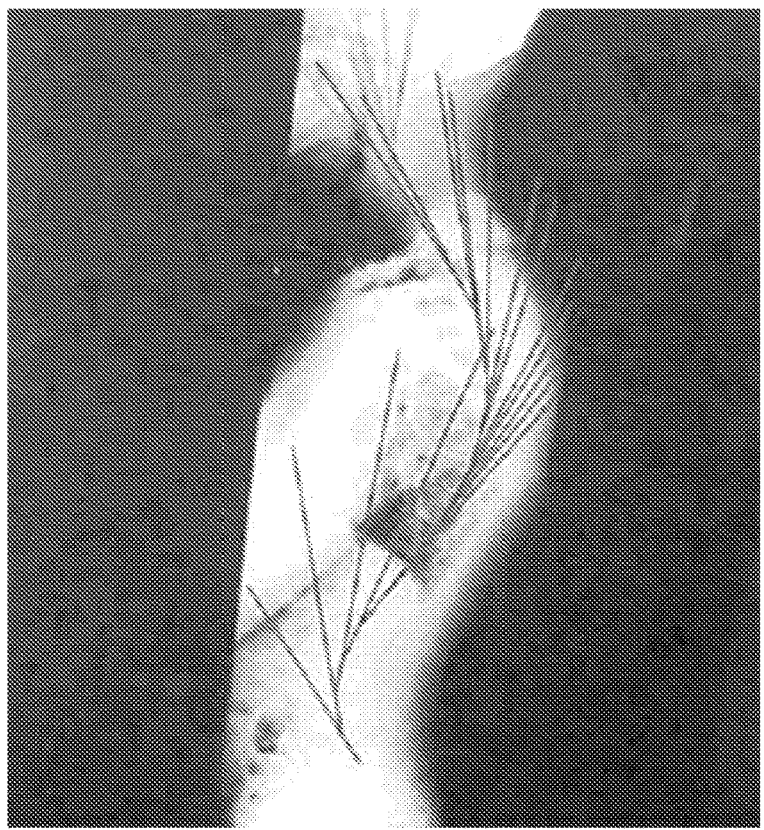
FIG. 9 is the radiographic image of FIG. 8 including digitized tangent lines according to an embodiment.
Figure 10:
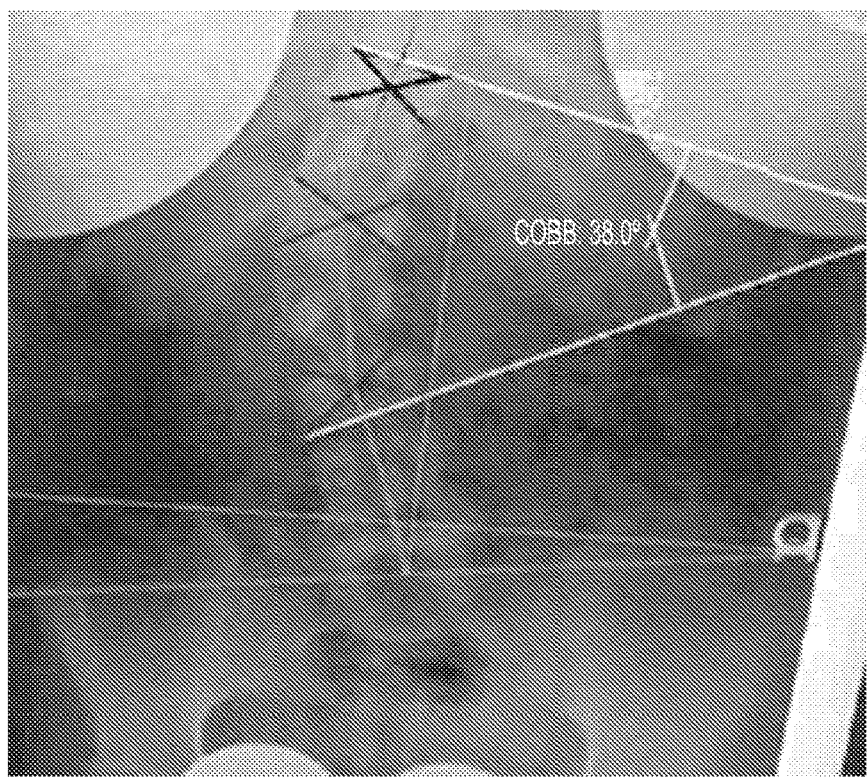
FIG. 10 is a radiographic image of a lumbar portion of the human spine from a dorsal viewpoint showing an overlay of data analysis points.

Alternative embodiments are illustrated in FIGS. 7, 8, 9, and 10. In particular, FIG. 7 illustrates a dorsal view of a cervical portion of the spine of a subject along with data analysis points and the normal line overlaid thereon. FIG. 8 illustrates a lateral view of a whole spine of a subject along with data analysis points and the normal line overlaid thereon. FIG. 9 illustrates tangent or endplate lines of the vertebrae overlaid on the image of FIG. 8. And FIG. 10 illustrates a dorsal view of a lumbar portion of the spine of a subject along with data analysis points and associated normal lines (in this case, the Cobb and Ferguson methods).

Specific elements of the disclosed systems and methods are described in further detail below with respect to the digitization, calculation and anatomical prediction features and the application of machine learning algorithms to these processes.

Digitization

The display screen in the several embodiments is preferably a touch screen for the purpose to quickly identify coordinates of the selected anatomical landmarks of the body image displayed on the screen, e.g., to digitize the anatomical landmarks for calculation of linear distances by the programmed computer of the device. These features advantageously reduce the time for measuring the dimensions and the accuracy, without the need for external equipment or special facilities.

The display and measurement according to embodiments use a software environment that provides visual display elements (views) that can be nested inside of one another; allowing one element to surround or envelope another. For example, the iOS operating system provides the UIView element (including UIView derivatives). For real-time cropping, requires a display screen that renders the views and any changes to the views (including size, scale, rotation, color, brightness, etc.).

1. Create two views, nested inside one another.
2. Load an image into the software (from a camera, disk drive, computer memory, etc)
3. Using the programming interface to assign the image to the inner view.
4. Optionally, use the programming interface to scale the inner view to be larger than the outer view.
5. Optionally, use the programming interface to adjust the location of the views so the inner view's boundaries extend past the outer view equally in all directions.
6. Regardless of completing step 4 and 5, allow the user to manipulate the inner view's size, scale, and location while keeping the outer view fixed in both size, scale, and location. Manipulation may occur by tracking the user input through any computer input device. For example, on the iOS operating system manipulation could be tracked by custom touch-screen readings or standard pinch-and-zoom features.
7. After user manipulation has completed (indicated by an arbitrary user action or input; for example pressing a "Done" button) use the programming interface to read the current size and position of both the inner and outer views.
8. Use the programming interface to capture the portion of the inner view image that is currently within the outer view's boundaries. Any portion of the inner view that extends past the outer view's boundaries will be cropped and discarded.
9. The programming interface may require the cropping boundary to be pre-calculated. The cropping boundary is used by the programming interface and applied to the original image to produce a new image from a portion of the original. The cropping boundary can be calculated with simple arithmetic:
    calculate (or read from the programming interface) the final offset distance between the inner view and outer view's center points,
    calculate (or read from the programming interface) the final resizing scale applied to the inner view,
    use the offset divided by the scale to determine the origin of the cropping boundary,
    use the fixed size of the outer view divided by the scale to determine the dimensions of the cropping boundary,
    for example, the X coordinate of a cropping boundary calculated in the iOS operating system would be: x=outerview.contentOffset.x/outerview.zoomScale; and the width of the cropping boundary would be: width=outerview.frame.width/outerview.zoom Scale.

As an example of calculating the cropping boundary, assume the following:
An image of size 460×460
An outer view of size 300×400
The user has manipulated the inner image view to move it an arbitrary direction and scaled to be twice as large. The result of the manipulation is an image with effective size of 920×920 (×2 scale) with an offset of 195 in the X coordinate direction and 289 in the Y coordinate.
The X coordinate of the cropping box would be 195/2=97.5 and the width of the cropping box would be 300/2=150.
For reference, the Y coordinate in this example would be 144.5 and the height 200.
The programming interface should produce a new image from the region of the original image with top left corner at 97.5, 144.5, width of 150 and height of 200.

Pixel distance measurement uses an image of an object cropped in a manner that the top and bottom of the object are at the edges of the top and bottom of the image, and the physical height of the object must be known. Requires a software environment that can interpret image data and provide pixel dimensions of the image.
1. Load the image into the software (from a camera, disk drive, computer memory, etc.)
2. Use the programming interface to read the pixel height of the image
3. Divide the known height of the object by the pixel height reading to determine the ratio of pixels to physical distance
4. The ratio can be used to calculate and convert any distance of pixels to physical distances by multiplying the ratio and the pixel distance For example, given an image that is 1000 pixels in height and an object that is known to be 60 inches in height we can calculate:

Each pixel represents 0.06 physical inches: 60/1000=0.06
A distance of 250 pixels represents 15 physical inches: 0.06×250=15

Calculation & Anatomical Prediction

Examples of known mathematical formulae useful in the several embodiments include, but are not limited to, the normal elliptical model, the Cobb method, and traditional chiropractic and orthopedic lines of mensuration.

Other models include the CBP® Ideal Spinal Model, the Geometrical Considerations model, and Dempster's Body Segment Parameter Data for 2-D Studies, as discussed in U.S. Patent Publication No. 2008/0009773 to Harrison et al., which is hereby incorporated by reference in its entirety.

Application of Machine Learning Algorithms

Disclosed embodiments may further include machine learning algorithms implemented on specialized computers or computer systems for executing the acquisition, digitization, calculation and anatomical prediction functions. In this regard, the algorithms may be used for automatically placing points for postural analysis using commercial or open source tools; for example, face detection to determine the points for the eyes, or joint detection for measurement of limbs. Machine learning algorithms may be used for determining the outer boundaries of a body part in an image, assisting with the measuring of specific body areas (i.e., waist, neck, etc.), and mathematically processing a large dataset of known measurements, in order to create a regression formula that will augment known measurement formulas or those disclosed herein. Machine learning algorithms may also be used in optimizing calculations and increasing the precision and accuracy of predictive measurement algorithms.

How effectively a machine learning algorithm can be trained may be related to how well the data is classified or labeled before it is used in a training procedure. Classifiers play an important role in the analysis of radiographic images of the human body. In embodiments, classifiers are used to classify the body dimensions such as, for example, body features, lengths, widths, etc., based on the relevant extracted body portions from the images. To develop a procedure for identifying images or videos as belonging to particular classes or categories (or for any classification or pattern recognition task), supervised learning technology may be based on decision trees, on logical rules, or on other mathematical techniques such as linear discriminant methods (including perceptrons, support vector machines, and related variants), nearest neighbor methods, Bayesian inference, neural networks, etc.

Generally, classifiers require a training set consisting of labeled data, i.e., representations of previously categorized media items (e.g., body dimensions), to enable a computer to induce patterns that allow it to categorize hidden media items. Generally, there is also a test set, also consisting of labeled data that is used to evaluate whatever specific categorization procedure is developed. In many cases, the test set is disjoint from the training set to compensate for the phenomenon of overfitting. In practice, it may be difficult to get large amounts of labeled data of high quality. If the labeled data set is small, the only way to get any useful results at all may be to use all the available data in both the training set and the test set.

To apply standard approaches to supervised learning, the media segments (body dimensions) in both the training set and the test set must be represented in terms of numbers derived from the images, i.e., features. The relationship between features extracted for the purposes of supervised learning and the content of an image or video has an important impact on the success of the approach.

Figure 11:
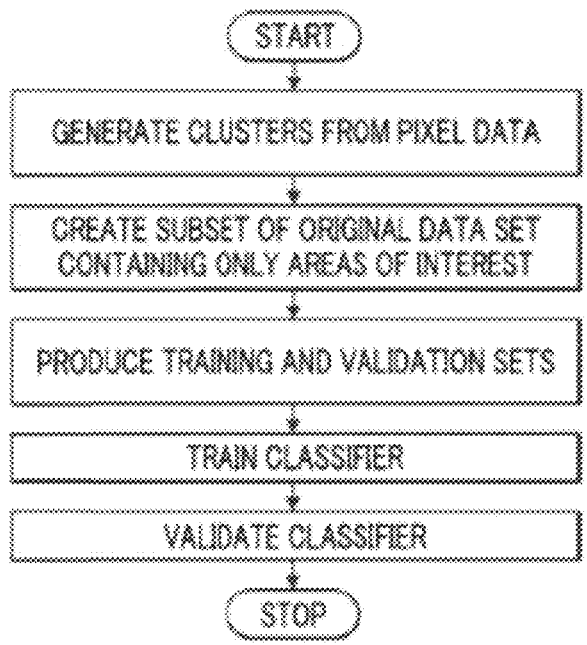
FIG. 11 illustrates a flowchart representation of a process of generating a set of image-based training data and using that training data to develop classifiers in accordance with an embodiment.

FIG. 11 illustrates a flowchart representation of a process of generating a set of image-based training data and using that training data to develop classifiers in accordance with an embodiment. As shown in the FIG. 11, the process begins with generation of clusters from an image's pixel data. Then, subsets of the original data set are created containing only areas of interest. Finally, training and validation data sets are created, and the classifiers are trained and validated.

The programmatic tools used in developing the disclosed machine learning algorithms are not particularly limited and may include, but are not limited to, open source tools, rule engines such as Hadoop®, programming languages including SAS®, SQL, R and Python and various relational database architectures.

Figure 12:
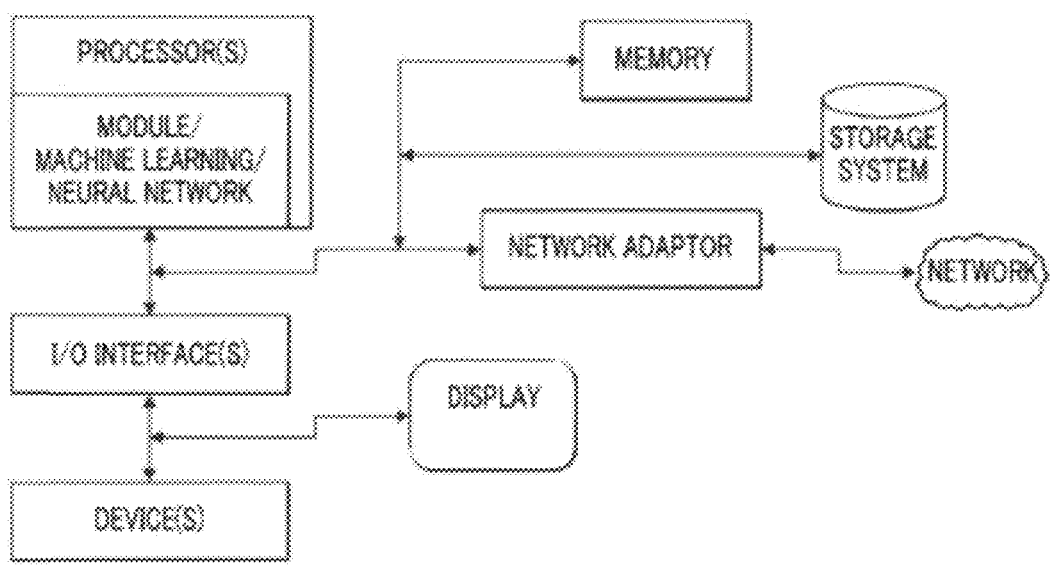
FIG. 12 illustrates a specialized computer or processing system that may implement machine learning algorithms according to disclosed embodiments.

FIG. 12 illustrates a schematic of an example specialized computer or processing system that may implement machine learning algorithms according to disclosed embodiments. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 12 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units, a system memory, and a bus that couples various system components including system memory to processor. The processor may include a module that performs the methods described herein. The module may be programmed into the integrated circuits of the processor, or loaded from memory, storage device, or network or combinations thereof.

The computer system communicates with external devices such as a radiographic system or traditional digital camera and may also communicate with one or more external devices such as a keyboard, a pointing device, a display, and the like, one or more devices that enable a user to interact with computer system, and/or any devices (e.g., network card, modem, etc.) that enable computer system to communicate with one or more other computing devices. Such communication can occur via Input/Output (I/O) interfaces. The computer system can communicate with one or more networks such as a local area network (LAN), a general wide area network (WAN), and/or a public network (e.g., the Internet) via network adapter.

The above-described machine learning techniques are further described in the following non-limiting example. By way of example, images from multiple subjects may be stored in a database along with a multitude of image-related data including all relevant measurements, digitized points, calculated parameters and predicted parameters. These data sets may then be used to create training data sets that are tested and validated. Subsequent images processed may then be analyzed according to the algorithms developed (i.e., the rules) and the digitized points may be set according to the rules. The relevant calculations and predictions may then be based upon these digitized points and other hierarchal rules known to be particularly relevant to characteristic classifications of the image (e.g., weight, age, gender, body type, etc.). In turn, each subsequent image further trains the machine learning algorithms by validating, i.e., weighting, scoring, updating, etc. The result is a machine learning paradigm that automates and optimizes the anatomical prediction process disclosed herein in ways not conventionally known.

In embodiments, anatomical landmark points may be automatically extracted using computer algorithms trained using supervised machine learning techniques. Examples of common machine learning methods for anatomical landmark point detection include, but are not limited to, Active Shape Model (ASM), Active Appearance Model (AAM), Deformable Part Models and Artificial Neural Networks. In some embodiments, open source algorithms such as OpenPose may be used for anatomical landmark points detection. In all of these methods, a set of training images with annotated landmark points are used to build models. Once a model is trained and validated on a dataset, it is applied to detect landmark points on novel images. In some practice, the training, validation, and test image datasets are separated. Separate models may be trained and used to detect and extract anatomical landmark points in frontal, side, and other views. Some models may accommodate variations in camera view angles.

The neural network may be a deep convolutional neural network. The neural network may be a deep neural network that comprises an output layer and one or more hidden layers. In embodiments, training the neural network may include: training the output layer by minimizing a loss function given the optimal set of assignments, and training the hidden layers through a back propagation algorithm. The deep neural network may be a Convolutional Neural Network (CNN).

Figure 13:
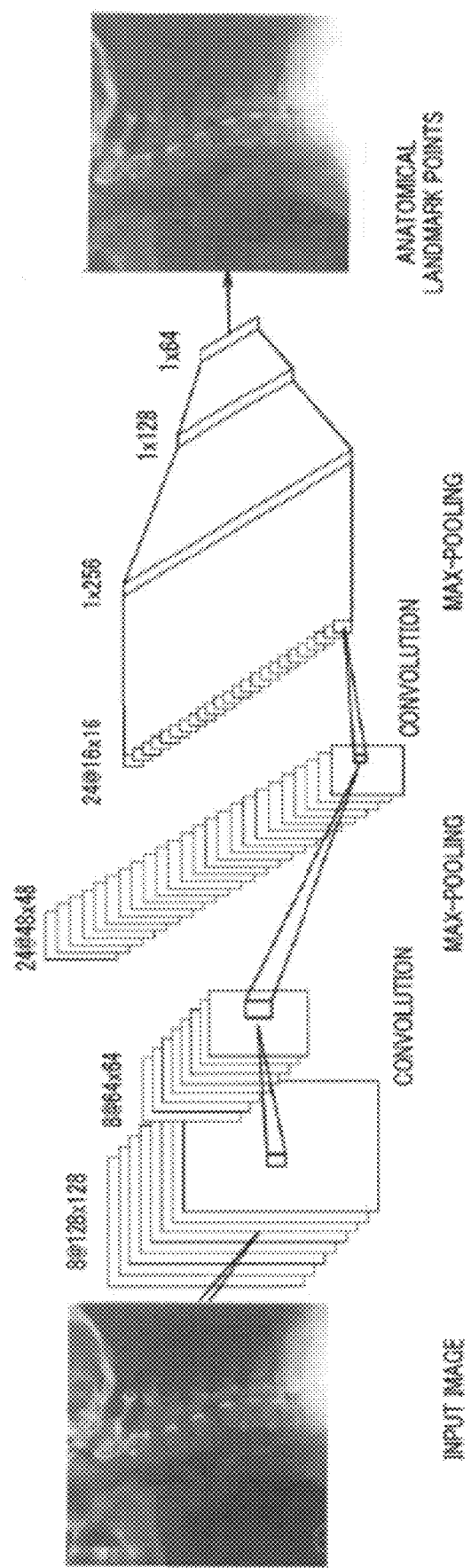
FIG. 13 illustrates a machine learning algorithm according to an embodiment.

In a CNN-based model, a set of filters are used to extract features from images using convolution operation. Training of the CNN is done using a training dataset containing images and landmark points, which determines the trained values of the parameters/weights of the neural network. FIG. 13 depicts a CNN architecture for learning landmark points. As seen in FIG. 13, the CNN includes multiple layers. A convolutional layer may include 8 128×128 kernels feeding into 2×2 pooling-layer. The pooling layer then feeds into another convolutional layer including 24, 48×48 kernels feeding into 2×2 pooling-layer. Further layers include fully-connected layers 1×256.

In some CNN models, the numbers of the CNN layers and fully connected layers may vary. In some network architectures, residual pass or feedbacks may be used to avoid a conventional problem of gradient vanishing in training the network weights. The network may be built using any suitable computer language such as, for example, Python or C++. Deep learning toolboxes such as TensorFlow, Caffe, Keras, Torch, Theano, CoreML, and the like, may be used in implementing the network. These toolboxes are used for training the weights and parameters of the network. In some embodiments, custom-made implementation of CNN and deep learning algorithms on special computers with Graphical Processing Units (GPUs) are used for training, inference, or both. The inference is referred to as the stage in which a trained model is used to infer/predict the testing samples. The weights of a trained model are stored in a computer disk and then used for inference. Different optimizers such as the Adam optimization algorithm, and gradient descent may be used for training the weights and parameters of the networks. In training the networks, hyperparameters may be tuned to achieve higher recognition and detection accuracies. In the training phase, the network may be exposed to the training data through several epochs. An epoch is defined as an entire dataset being passed only once both forward and backward through the neural network.

Figure 14:
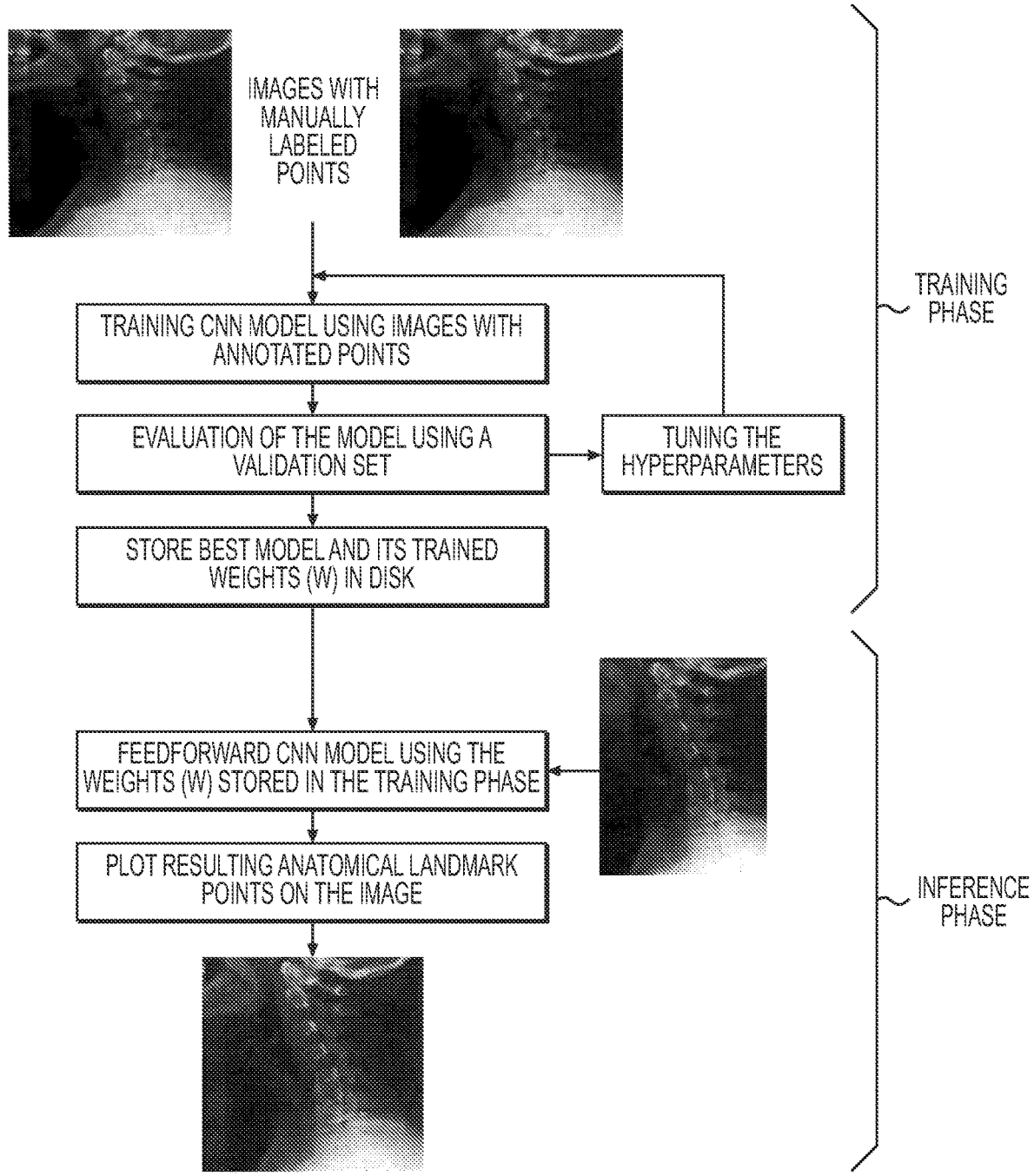
FIG. 14 illustrates a process executed by a machine learning algorithm according to an embodiment.

An example application of the CNN model according to embodiments is illustrated in FIG. 14. As seen in FIG. 14, training images are marked with annotated points of measurement. The CNN model is trained based on the annotated points and weighting factors, as described herein. Evaluation of the model using a validation set is conducted to validate the trained model. At this stage, hyperparameters may be tuned and the model retrained based on the tuned parameters. In any event, the best performing trained model is identified and stored along with the relevant weighting factors. Once the training phase is complete, the process proceeds to the inference phase where the trained and validated model is applied to a captured radiographic image of a body of a person and the resulting anatomical landmark points are plotted on the image.

In some embodiments, a CNN-based network may be used for detection of the body structure (e.g., the spine) silhouette. The detected body in original images is then used in training or testing the network responsible for anatomical landmark points' detection. In some networks, CNN-based methods such as You Only Look Once (YOLO) or DarkNet may be used for detection of the body structure silhouette. A bounding box may be used to show the position of a detected body structure in images. These two networks (body detection and anatomical landmark point detection)

may be merged together. In this case, instead of training two separate but cascaded networks (a network responsible for human body detection in images and a network responsible for landmark point detection), one combined network is trained and utilized for both body detection and landmark extraction.

The network can be trained using a transfer learning mechanism. In transfer learning, the network's weights are initially trained using a different image database than the posture image database to learn the digitized points. Then, this pre-trained network is retrained further using the images in posture database. The CNN architecture can be 3-dimensional to handle 3D image data.

It should be understood, of course, that the foregoing relates to exemplary embodiments of the invention and that modifications may be made without departing from the spirit and scope of the invention as set forth in the following claims. For example, anatomical predictions can include other predictions than those in the specific embodiments described herein without departing from the scope of the embodiments as recited in the appended claims. Likewise, the digital display screen need not be a touch screen display as in the example embodiments but otherwise allowing, as by clicking a mouse, for example, to demark various anatomical landmarks thereon in accordance with the invention, as will be readily understood by the person skilled in the art.

What is claimed is:

1. A method for use of machine learning in computer-assisted anatomical prediction, the method comprising:
    selecting a portion of a radiographic image of at least one of a spine and a pelvis of a person displayed on a screen;
    identifying with a processor parameters in a plurality of training images to generate a training dataset, the training dataset having data linking the parameters to respective training images;
    training at least one machine learning algorithm based on the parameters in the training dataset and validating the trained machine learning algorithm;
    automatically detecting with the processor a plurality of digitized points using the validated machine learning algorithm, each digitized point corresponding to an anatomical point on the at least one of the spine and the pelvis in the selected portion of the radiographic image;
    determining anatomical dimensions of at least a portion of the at least one of the spine and the pelvis of the person in the displayed image using the anatomical points and a scale factor for the displayed image; and
    making an anatomical prediction of the person based on the determined anatomical dimensions and a known morphological relationship,
    wherein the anatomical prediction is a linear translational movement or angular rotational movement measure of a skeletal alignment or displacement.

2. The method of claim 1, wherein training the machine learning algorithm includes weighting the parameters in the training dataset and validating the machine learning algorithm includes storing a best version of the machine learning algorithm and the corresponding weighted parameters.

3. The method of claim 1, wherein using the machine learning algorithm comprises:
    generating clusters from pixel data in the displayed image;
    creating subsets of the pixel data containing only areas of interest;
    identifying at least one classifier in the subsets of the pixel data;
    generating a training dataset based on the at least one classifier identified in the subsets of the pixel data; and
    validating the at least one classifier in the training dataset.

4. The method of claim 1, wherein parameters in the image of the person displayed on the screen are used to further train and validate the machine learning algorithm by updating corresponding parameters in the training dataset.

5. The method of claim 1, wherein the parameters are at least one selected from the group consisting of weight, age, gender, body type, and body measurement.

6. The method of claim 5, wherein the body measurement is a measurement selected from the group consisting of neck, overarm, chest, waist, hips, sleeve, and outseem.

7. The method of claim 1, wherein the machine learning algorithm is at least one selected from the group consisting of an active shape model, an active appearance model, a deformable part model, and a neural network.

8. The method of claim 1, wherein the machine learning algorithm is a deep convolutional neural network.

9. The method of claim 8, wherein training the deep convolutional neural network includes training an output layer by minimizing a loss function given an optimal set of assignments, and training hidden layers through a back propagation algorithm.

10. The method of claim 1, wherein the training step includes using a trained model to infer testing samples by weighting the plurality of training images relative to the parameters in the source dataset.

11. The method of claim 10, wherein the weighting includes optimizing using the plurality of training images relative to the parameters using an Adam optimization algorithm or a gradient descent algorithm.

12. The method of claim 1, wherein the known morphological relationship is at least one of a normal elliptical line, the Cobb method, traditional lines of mensuration in orthopedics, and radiographic genre.

13. The method of claim 1, wherein the machine learning algorithm is trained using a transfer learning process comprising using weights from corresponding parameters trained using a separate image dataset to learn the digitized points.

14. The method of claim 1, wherein the radiographic image is an image of at least a portion of the spine.

15. The method of claim 1, wherein the anatomical prediction is a deviation from a normal line.

16. The method of claim 1, wherein the scale factor is a ratio of pixel to distance.

17. The method of claim 1, further comprising plotting the plurality of digitized points on the image of the at least one of the spine and the pelvis displayed on the screen.

18. The method of claim 1, further comprising displaying the anatomical prediction on the image of the at least one of the spine and the pelvis displayed on the screen.

19. The method of claim 1, wherein the anatomical dimensions include at least one of linear and angular dimensions.

20. The method of claim 1, wherein the skeletal alignment or displacement is a segmental vertebral hyper-extension or hyper-flexion buckling of a sagittal curve in a lateral view.

21. A system for use of machine learning in computer-assisted anatomical prediction, the system comprising:
    a memory configured to store at least one machine learning algorithm and datasets;
    a processor programed to:
        (i) input a selection of a portion of a radiographic image of at least one of a spine and a pelvis of a person displayed on a screen;

(ii) identify parameters in a plurality of training images to generate a training dataset, the training dataset having data linking the parameters to respective training images;
(iii) train the machine learning algorithm based on the parameters in the training dataset and validate the trained machine learning algorithm;
(iv) automatically detect a plurality of digitized points using the validated machine learning algorithm, each digitized point corresponding to an anatomical point on the at least one of the spine and the pelvis in the selected portion of the radiographic image;
(v) determining anatomical dimensions of at least a portion of the at least one of the spine and the pelvis of the person in the displayed image using the anatomical points and a scale factor for the displayed image; and
(vi) make an anatomical prediction of the person based on the determined anatomical dimensions and a known morphological relationship,
wherein the anatomical prediction is a linear translational movement or angular rotational movement measure of a skeletal alignment or displacement.

22. A non-transitory computer readable storage medium having stored therein a program to be executable by a processor for use of machine learning in computer-assisted anatomical prediction, the program causing the processor to execute:

inputting a selection of a portion of a radiographic image of at least one of a spine and a pelvis of a person displayed on a screen;
identifying with a processor parameters in a plurality of training images to generate a training dataset, the training dataset having data linking the parameters to respective training images;
training at least one machine learning algorithm based on the parameters in the training dataset and validating the trained machine learning algorithm;
automatically detecting with the processor a plurality of digitized points using the validated machine learning algorithm, each digitized point corresponding to an anatomical point on the at least one of the spine and the pelvis in the selected portion of the radiographic image;
determining anatomical dimensions of at least a portion of the at least one of the spine and the pelvis of the person in the displayed image using the anatomical points and a scale factor for the displayed image; and
making an anatomical prediction of the person based on the determined anatomical dimensions and a known morphological relationship,
wherein the anatomical prediction is a linear translational movement or angular rotational movement measure of a skeletal alignment or displacement.

* * * * *